(12) United States Patent
Colliec-Jouault et al.

(10) Patent No.: US 6,828,307 B1
(45) Date of Patent: Dec. 7, 2004

(54) LOW MOLECULAR WEIGHT SULPHATED POLYSACCHARIDE TO OBTAIN A MEDICINE WITH ANTITHROMBOTIC ACTIVITY

(75) Inventors: Sylvia Colliec-Jouault, Nantes (FR); Patrick Durand, Reze (FR); Anne-Marie Fischer, Paris (FR); Jacqueline Jozefonvicz, Lamorlaye (FR); Didier Letourneur, Le Plessis Robinson (FR); Jean Millet, Corcelles les Citeaux (FR)

(73) Assignees: Institut Francais de Recherche Pour L'Exploitation de la Mer, Issy les Moulineaux (FR); Centre National de La Recherche Scientifique, Paris (FR); Universite Rene Descartes, Paris (FR)

( * ) Notice: Subject to any disclaimer, the term of this patent is extended or adjusted under 35 U.S.C. 154(b) by 0 days.

(21) Appl. No.: 10/069,913

(22) PCT Filed: Sep. 1, 2000

(86) PCT No.: PCT/FR00/02421

§ 371 (c)(1), (2), (4) Date: Jul. 12, 2002

(87) PCT Pub. No.: WO01/15654

PCT Pub. Date: Mar. 8, 2001

(30) Foreign Application Priority Data

Sep. 1, 1999 (FR) .......................................... 99 10965

(51) Int. Cl.$^7$ ............................................ A61K 31/726
(52) U.S. Cl. .............................. 514/54; 514/56; 514/59
(58) Field of Search ............................. 514/54, 56, 59

(56) References Cited

U.S. PATENT DOCUMENTS

| | | | | |
|---|---|---|---|---|
| 4,533,549 A | * | 8/1985 | Lasker | 514/56 |
| 4,713,373 A | * | 12/1987 | Bayol et al. | 514/56 |
| 5,321,133 A | * | 6/1994 | Colliec et al. | 536/118 |
| 5,458,568 A | * | 10/1995 | Racchini et al. | 604/19 |

FOREIGN PATENT DOCUMENTS

| | | |
|---|---|---|
| EP | 0 403 377 A1 | 12/1990 |
| EP | 0 408 770 A1 | 1/1991 |
| EP | 0 849 280 A2 | 6/1998 |
| WO | WO 97/08206 | 3/1997 |

OTHER PUBLICATIONS

J. Millet; Antithrombotic and Anticoagulant Activities of a Low Molecular Weight Fucoidan by the Subcutaneous Route; Laboratories Fournier; Mar. 1999; pp. 391–395; vol. 81, No. 3; Thromb Haemostas.

T.A. McCaffrey, et al; Fucoidan Is A Non–Anticoagulant Inhibitor Of Intimal Hyperplasta; Biochemical And Biophysical Research Communications; Jan. 1, 1992; pp. 773–781; vol. 184, No. 2; Department of Medicine, Pathology and Cell Biology and Anatomy.

S. Mauray et al; "Venous Antithrombotic And Anticoagulant Activities Of A Fucoidan Fraction"; Thrombosis And Haemostasis, DE, Stuttgart; vol. 74, No. 5, Nov. 1, 1995; pp. 1280–1285.

V Grauffel et al; "New Natural Polysaccharides With Potent Antithrombic Activity: Fucans From Brown Algae"; Biomaterials, GB, Elsevier Science Publishers BV., vol. 10, No. 6, Aug. 1, 1989; pp. 363–368.

Logeart et al; "Fucans, sulfated polysaccharides extracted from brown seaweeds, inhibit vascular smooth muscle cell proliferation. I. Comparison with heparin for antiproliferative activity, binding and internalization"; Eur. J. Cell. Biol.; vol. 74, Dec. 1997, pp. 376–390.

Colltec et al; A Low Molecular Weight Fucoida Fraction From The Brown Seaweed *Pelvetia Canaliculata*; Phytochemistry, vol. 35, No. 3, 1994, pp. 697–700.

* cited by examiner

*Primary Examiner*—Samuel Barts
*Assistant Examiner*—Leigh C. Maier
(74) *Attorney, Agent, or Firm*—Alston & Bird LLP

(57) ABSTRACT

The invention concerns the use of a sulphated polysaccharide capable of being obtained by radical depolymerization of a raw fucan derived from Pheophyceae, said polysaccharide having a molar mass not more than 10,000 g/mol, to obtain a medicine for preventing or treating vascular thrombosis, in particular venous thrombosis, arterial thrombosis and arterial restenosis.

12 Claims, No Drawings

LOW MOLECULAR WEIGHT SULPHATED POLYSACCHARIDE TO OBTAIN A MEDICINE WITH ANTITHROMBOTIC ACTIVITY

The present invention relates to the use of a sulfated polysaccharide with a molar mass of less than or equal to 10,000 g/mol, which can be obtained by radical depolymerization of a crude fucan derived from Phaeophyceae, for producing a medicinal product with activity against arterial thrombosis and against arterial restenosis.

Thrombosis consists of the formation of a clot (thrombus) in the circulatory system, this clot obstructing the lumen of the vessel in which it forms. It is the consequence of the pathological activation of the physiological phenomena of haemostasis, i.e. of the phenomena which contribute to the prevention and arrest of bleeding.

Thrombosis brings into a play a complex process involving the activation, in cascade, of various factors, resulting in the formation of thrombin, which is a key clotting enzyme, and then in fibrin formation. The formation of the thrombus begins with adhesion of the platelets to the subendothelial connected tissue, exposed by a lesion of the vascular endothelium. The platelets aggregate with one another and the aggregate becomes surrounded by a fibrin network which also traps white blood cells and red blood cells, forming the thrombus.

Arterial thrombosis differs from venous thrombosis in that, most commonly, it occurs on an artery in which there is a lesion due to the presence of an atheroma plaque; this lesion is also characterized by the proliferation and the migration toward the intima of the smooth muscle cells of the media. Arterial thrombosis often occurs when the atheroma plaque ruptures, with loss of continuity of the vascular endothelium. The adhesion and aggregation of platelets plays a primordial role in the phenomenon of arterial thrombosis.

The entire process of response to the lesion of an artery involves many cellular biological phenomena which involve modifications of the phenotype of smooth muscle cells (SMCs), and also the expression of growth factors which promote the proliferation of endothelial cells.

In the treatment of venous thrombosis, anticoagulants, in particular heparin, are conventionally used, which have the property of inhibiting thrombin and its formation.

Heparin is a sulfated polysaccharide consisting of units of glucosamine and of uronic acids which are 1,4-linked, in which the sulfate groups are present on the amine function of the glucosamine and/or on alcohol functions of the glucosamine and of the uronic acid. This polysaccharide, the anticoagulant properties of which are well known, is currently widely used in the treatment of thrombotic accidents. However, heparin has very significant side effects (bleeding, risk of immunoallergic thrombopenia) and it is relatively ineffective in arterial thrombosis. In addition, the animal origin of this product may cause a potential risk of contamination with unconventional infectious agents.

Techniques of chemical or enzymatic depolymerization have made it possible to produce, from NFH (nonfractionated heparin, the molecular weight of which is approximately 15,000 g/mol), polysaccharide chains of low molecular weight, i.e. of molecular weight of between 2000 and 10,000 g/mol, named LMWHs (low molecular weight heparins). Many LMWHs have been synthesized and are in particular marketed under the names Enoxaparin®, Reviparin®, Dalteparin®, Fraxiparin®, Tinzaparin®, Certoparin®, Opocrin®, Parnaparin® etc.

Clinical studies have shown that the effectiveness of the LMWHs in the prophylaxis of venous thromboembolic accidents is identical to, if not greater than, that of NFH. However, the LMWHs do not abolish the hemorrhagic risk and can cause, just as NFH, although less frequently, immunoallergic thrombopenia.

Furthermore, it has been shown, in particular by M. Lerch et al. (European Heart Journal, August 1998, 19, 495) and H. Rickli et al. (European Heart Journal, August 1998, 19, 470), that LMWHs (Reviparin® and Fraxiparin® respectively') are ineffective in combating restenosis after angioplasty, i.e. the phenomenon of reappearance of a stricture of the lumen of an artery linked to the involvement of a balloon catheter in vascular surgery.

Sulfated polysaccharides other than heparins exist, for example fucans. These sulfated polysaccharides, of high molecular weight (100 to 800 kDa), are present in the cell walls of the thalli of brown algae. They are polymers of sulfated L-fucose and may also contain D-xylose, D-galactose, D-mannose and uronic acids, the latter not being sulfated, contrary to those of heparin. Fucans also differ from heparin in that they do not comprise any amino sugars.

Fucans have various properties which make their use in many therapeutic domains particularly advantageous.

It has in particular been shown that fractions of low molar mass fucan, obtained by acid hydrolysis as described in European patent 0 403 377, have an anticoagulant (S. Colliec et al., Thromb. Res., 1991, 64, 143–154) and antithrombotic activity, when given intravenously (S. Mauray et al., Thrombosis and Haemostasis, 1995, 74(5), (280–1285) or subcutaneously (J. Millet et al., Thrombosis and Haemostasis, 1999, 81, 391–395) comparable to that of the low molecular weight heparins.

It has also been shown that these same fucan fractions are capable of inhibiting, like heparin, the growth of vascular smooth muscle cells in culture (D. Logeart et al., Eur. J. Cell. Biol., 1997, 74, 376–384 and 385–390). The effects observed are reversible, are not related to a cytotoxic action and depend on the concentration of the compound in the culture medium. This antiproliferative effect on the growth of smooth muscle cells appears to be specific since, at these concentrations, no inhibition is observed on the growth of fibroblast lines, and these compounds are observed to be capable of potentiating endothelial cell growth in culture (J. L. Giraux et al., Eur. J. Cell. Biol. 1998, 77, 352–359).

Giraux et al. have shown, in Thromb. Haemost., 1998, 80, 692–695, that the same fucan fractions, obtained by acid hydrolysis according to the protocol described in European patent 0 403 377, induce, in vitro, the release of TFPI (Tissue Factor Pathway Inhibitor) by human umbilical cord vein endothelial cells, this being an effect which may contribute to the antithrombotic action of these fucan fractions.

In addition, it has been shown, in Patent application EP 0 846 129, that fucan fractions, obtained by radical depolymerization of a fucan from Phaeophyceae in the presence of a metal catalyst and of hydrogen peroxide, and having a molar mass of less than or equal to 10,000 g/mol, conserve, in vitro, the anticoagulant properties of crude fucan. Such fucan fragments, obtained by radical depolymerization of a high molecular weight fucan, are different, with respect to their chemical structure, from fucan fragments obtained by acid hydrolysis of a crude fucan, as demonstrated in Patent application EP 0 846 129.

Besides NFH, LMWHs and fucans, other anticoagulants have been described for their antithrombotic action (inhibition of the formation of the thrombus and/or of its growth): these are in particular heparinoids (mixture of low molecular weight glycosaminoglycans, for example Organe marked by Organon Inc.), antivitamins K and hirudins. Hirudins, for example Lepirudin (Refludan®) marketed by Behrinwerke AG—Hoechst Marion Roussel or Desirudin (Revasc®) marketed by Novartis—Rhône Poulenc Rorer, can cause, in the same way as nonfractionated heparin, a considerable hemorrhagic risk.

Two classes of compounds can be used or are being studied in arterial thrombosis (Samama M. M. and Desnoyer P. C., "*Les bases pharmacologiques des traitements antithrombotiques—Agents antithrombotiques actuels et futurs*" [*The pharmacological bases of antithrombotic treatments— Current and future antithrombotic agents*], 1995, publisher Masson): there are anti-platelet aggregation agents, for example acetylsalicylic acid, dipyridamole, ticlopidine, clopidogrel and anti-GPIIb/IIIa antibody, and fibrinolytics (streptokinase, urokinase, etc.), which dissolve the clot by activation of the fibrinolytic system and release of plasmin (proteolytic enzyme capable of rapidly lysing the fibrin clot).

The use of these compounds must often be combined with an endoscopic intervention in order to widen the lumen of the narrowed artery, such as an angioplasty. Now, these treatments are not sufficiently effective in the medium term, since restenosis of the arteries in which occlusions have been removed in this way frequently occurs, even within a few months following the treatment.

Thus, it appears that the antithrombotic agents described above do not make it possible to effectively prevent or treat an arterial thrombosis or a restenosis, which is an essential problem after an angioplasty. Following such surgery, the endothelium exhibits dysfunction compared to the endothelium of origin. The parietal attack induced by this surgery may result in a phenomenon of decompartmentalization: loss of the endothelium and direct communication between the blood compartment and the smooth muscle cells. The wall responds to this attack via a process which combines migration, proliferation, destruction and secretion of extracellular matrix, via the smooth muscle cells positioned in the intima, followed by regrowth of the endothelium, which contributes to its thickening and therefore to the stricture of its lumen. This phenomenon of parietal cicatrization may contribute to the pathological condition itself, like anastomotic stenoses on vascular prostheses and restenoses after endoluminal dilation.

In view of the current state of the art, there is therefore a need for an agent with activity against arterial thrombosis and arterial restenosis.

The inventors have thus given themselves the aim of providing an agent which may be used for producing a medicinal product with activity against arterial thrombosis and arterial restenosis, said medicinal product:

having activity against vascular thrombosis, in particular against venous thrombosis, and particularly advantageously against arterial thrombosis, this being when it is administered parenterally, not presenting any major hemorrhagic risk, not having the potential risk of viral contamination related to products of animal origin, making it possible to obtain prevention of arterial occlusion in the context of prevention of restenosis, in particular following an angioplasty.

The inventors have now shown that, unexpectedly, these aims are achieved by using a sulfated polysaccharide which can be obtained by radical depolymerization of a crude fucan derived from Phaeophyceae, said polysaccharide having a molar mass of less than or equal to 10,000 g/mol.

A subject of the present invention is the use of a sulfated polysaccharide which can be obtained by radical depolymerization of a crude fucan derived from Phaeophyceae, said polysaccharide having a molar mass of less than or equal to 10,000 g/mol, for producing a medicinal product intended to prevent or treat vascular thrombosis.

Particularly advantageously, the use of such a sulfated polysaccharide makes it possible to obtain an antithrombotic effect which is not accompanied by a major hemorrhagic risk.

Said sulfated polysaccharide can be obtained as described in Patent application EP 0 846 129. By way of example, the type of Phaeophyceae from which said sulfated polysaccharide is derived is *Ascophyllum nodosum, Fucus vesiculosus, Pelvetia canaliculata* or *Undaria pinnatifida*.

Particularly advantageously, the plant origin of the polysaccharide used in the present invention eliminates any risk of viral contamination of the individual to which it is administered.

According to an advantageous embodiment of the use according to the invention, said medicinal product is intended to prevent or treat venous thrombosis.

According to another advantageous embodiment of the use according to the invention, said medicinal product is intended to prevent or treat arterial thrombosis, a process in which the formation of the thrombus and the platelet deposits play an important role.

According to an advantageous arrangement of this embodiment, said medicinal product is intended to prevent arterial restenosis, a phenomenon which is a precursor to arterial thrombosis.

Specifically, in the context of the prevention of arterial thrombosis, it is particularly advantageous to seek to prevent arterial restenosis, this being a pathological condition which, when it manifests itself, may result in a thrombosis of the artery.

The sulfated polysaccharide used in the present invention advantageously has a molar mass of less than 5000 g/mol.

According to another advantageous embodiment of the present invention, said medicinal product is intended to be administered parenterally, preferably intravenously or subcutaneously.

In rabbits, in an experimental model of venous thrombosis, after subcutaneous injection, the same antithrombotic activity is observed for doses of LMWH and of sulfated polysaccharide (polysaccharide which can be obtained by radical depolymerization of a crude fucan derived from Phaeophyceae, as described above) equal to 1 mg/kg and to 10 mg/kg, respectively, i.e. for a dose of sulfated polysaccharide 10 times greater than that of an LMWH.

If it is possible to extrapolate to humans, the daily doses of said medicinal product are preferably between 150 and 300 mg (preventive administration) or between 450 and 600 mg (curative administration) subcutaneously; it is clearly understood, however, that those skilled in the art will adjust the doses depending on the age, on the weight and on the pathological condition of the patient, in particular depending on the thrombogenic risk.

In the embodiment relating to the prevention of arterial restenosis, said medicinal product is advantageously intended to be administered locally, for example by endoparietal diffusion.

Endoparietal diffusion consists of local administration of the pharmaceutical composition, for example by means of a balloon. The repeated passage of the balloon, during the surgical intervention of angioplasty, has the effect of eliminating the endothelium and stressing the muscle cells and the extracellular matrix of the media. In response to the de-endothelialization, platelet aggregation will recur at the site of the lesion, locally releasing PDGF (Platelet Derived Growth Factor). In response to the medial stress, the intracellular FGF stored in the matrix will be released. These growth factors will induce the activation, migration and proliferation of the smooth muscle cells.

The technique of endoparietal diffusion allows endovascular topical distribution of the active principle present in said pharmaceutical composition. Various types of balloon may be used, such as catheters with dual balloons isolating an infusion chamber or gel-coated balloons, or nonoccluding catheters.

Besides the above arrangements, the invention also comprises other arrangements which will emerge from the following description, which refers to examples of measuring the antithrombotic activity, the hemorrhagic risk and the anticoagulant effect of sulfated polysaccharides obtained by depolymerization of a fucan from Phaeophyceae, and also to the study of the effects of these polysaccharides on platelet aggregation.

It should be clearly understood, however, that these examples are given only by way of illustration of the subject of the invention, of which they in no way constitute a limitation.

EXAMPLE 1

Antithrombotic Activity of Sulfated Polysaccharides Obtained by Depolymerization of a Fucan From Phaeophyceae 1. Preparation of the Low Molecular Weight Fucan and of its References In this example and in those which follow, unless otherwise indicated, the references for the low molecular weight fucan are as follows:
- the standard nonfractionated heparin (NFH) is a TERHORMON TH/023 heparin (150 IU/mg) supplied by Terdobliate (Novara, Italy). It has a mean molecular mass of approximately 15,000 g/mol;
- the low molecular weight heparin (LMWH) is supplied by Pharmacia (France) under the name Fragmine* (batch 94134, 2500 IU anti-Xa/0.2 ml). It has a mean molecular mass of approximately 5000 g/mol.

The required concentrations of NFH and of LMWH are obtained by dilution with physiological saline.

The low molecular weight fucan (LMWF) used is obtained by radical depolymerization of a fucan from Phaeophyceae (*Ascophyllum nodosum*) in accordance with the method described in Patent application EP 0 846 129. The protocol used is as follows:

Radical Depolymerization 25 liters of aqueous fucan extract, obtained according to the protocol described by Nishino et al. (Carbohydrate Research, 1989, 186, 119–129) adjusted for the alga *Ascophyllum nodosum*, are introduced into a reactor with a volume of 45 liters, equipped with a device for stirring at 100 rpm. The temperature is brought to and maintained at 60° C. 75 g of copper acetate (Fluka) are added, i.e. a copper acetate concentration of 0.02 M. The pH is adjusted to 7.5 with approximately 400 ml of 2 N sodium hydroxide (NaOH 400 g/l, Panréac). Hydrogen peroxide is then added at a concentration of 10 to 13% at a flow rate of 85 ml/minute, for 4 h.

Removal of the Copper

The reaction medium is filtered over glass microfiber filters, the pore diameter of which is 2.6 µm (Whatman filters, reference GF/D 1823-150), in order to remove the green-colored precipitate formed during the depolymerization reaction. The residual copper is then retained by passage over a resin (Chelex® 20, Biorad): the depolymerized extract is introduced, at a flow rate of 13 to 15 l/h, into a glass column, with a cross section of 113 cm$^2$, containing 5 liters of pre-passivated resin. The solution of depolymerized fucan leaving the column is decolorized and has a pH of between 10 and 11.

The resin used is then regenerated according to the operating conditions given by the manufacturer.

Diafiltration, Concentration and Lyophilization

The solution of depolymerized fucan obtained above is subjected to ultrafiltration on a Pellicon® (Millipore) system equipped with two 1 kDalton polysulfone membranes (Filtron). Conductivity is monitored throughout this process, using 10 volumes of osmosed water.

After having been concentrated down to a final volume of 4 to 5 liters, the product is lyophilized. The yield, calculated on the lyophilizate, is 27%.

Reduction With Borohydride 267 g of the depolymerized fucan obtained above (lyophilized fucan) are dissolved in 3 l of osmosed water and the solution is homogenized. 10 ml of this solution are taken for analysis of the fucan before the step of reduction of the terminal monosaccharides of the polysaccharide chains.

Separately, 202 g of sodium borohydride are dissolved in 3 l of water. The borohydride solution is then added to the fucan solution. The reaction is immediate and very effervescent. After 2 hours, the reaction is stopped by adding 10 N acetic acid (glacial acetic acid, Panréac) until a neutral pH is obtained. The volume of acid added is 400 ml.

After neutralization, the solution is filtered over glass microfibers (Whatman filter, reference GF/D 1822-290) and subjected to ultrafiltration/diafiltration on a Pellicon® system (Millipore) equipped with two polysulfone membranes with a cut-off threshold of 1 kDalton (Filtron). The initial volume is 9 l; the initial conductivity is 16.5 mS and falls to 3.5 mS at the end of the ultrafiltration/diafiltration. After concentrating down to 7.5 l, the product is successively filtered over filters with pore diameters of 2.6 µm (GF/D, Whatman), then 0.7 µm (GF/F, Whatman), and finally 0.2 µm (Whatman cellulose nitrate filters, reference 7182-09). The final volume to be lyophilized is 7.75 l. The overall yield of the reduction is 60%, this low value being due to the many manipulations performed during this step.

The total yield of the method for producing a low molecular weight fucan (depolymerization and reduction) is, consequently, 16.2%.

The reduction step does not modify the anticoagulant activity or the chemical composition of the fucan, as will be detailed below (cf. Table I).

Table I summarizes the characteristics of the product (depolymerized fucan) before and after the reduction step, namely its molar mass (Mc: chromatographic molar mass determined at the top of the peak), its polydispersity index (corresponding to the ratio $M_w/M_n$, with $M_w$: weight average molecular mass and $M_n$: number average molecular mass), and its content of neutral saccharides (fucose, galactose, xylose), of uronic acid and of sulfate ($SO_3Na$), and also the measurement of the anticoagulant activity of the product by APTT (Activated Partial Thromboplastin Time), expressed as amount of product added to 1 ml of PPP (Platelet-Poor Plasma) required to double the control clotting time (39 seconds).

The content of neutral saccharides was measured according to the technique described by Mopper et al. (environ.

Sci. Technol., 1992, 26, No. 1, 133–138). The other parameters were measured as indicated in Patent application EP 0 846 129.

It emerges from Table I that the reduction method described above, carried out after the radical depolymerization, makes it possible to obtain a low molecular weight fucan which is not very polydisperse, without modifying its chemical composition overall and without desulfating it.

TABLE I

|  | Fucan before depolymerization (aqueous extract) | Depolymerized fucan, before reduction | Depolymerized fucan, after reduction |
|---|---|---|---|
| Mc (g/mol) | >600,000 | <5000 | <5000 |
| Polydispersity index | 5 | 1.9 | 1.7 |
| Fucose (%) | 28.4 | 32.8 | 34.3 |
| Galactose (%) | 3.4 | 1.6 | 1.4 |
| Xylose (%) | 3.7 | 1.2 | 1.0 |
| Uronic acid (%) | 8.5 | 3.7 | 2.7 |
| SO$_3$Na (%) | 22.7 | 34.2 | 32.2 |
| APTT (anticoagulant activity) (μg/ml of PPP) | nd* | 25 | 25 |

*nd: not determined

2. Venous Thrombosis According to Wessler in Rabbits

Protocol

The experimental venous thrombosis is that of Wessler et al. (1959) using activated factor X (FXa) as a hypercoagulant (Mauray et al., Throm. Haemost., 1995, 74, 1280–5 and Millet et al., Throm. Haemost., 1992, 67, 176–9).

As described by Millet et al. (Throm. Haemost, 1999, 81, 391–395), the products are administered subcutaneously, a dose-effect study being carried out and the kinetics of the effect being measured.

Results

The LMWF has a dose-dependent activity which manifests itself from a dose of 2.5 mg/kg, with a significant decrease in the weight of the thrombi of close to 35%. This activity is close to 100% for a dose of 10 mg/kg.

Activities of 50%, 80% and 90% were obtained for respective doses of Fragmin of 80, 100 and 200 IU anti-Xa/kg (Millet et al., 1999, ibid.).

Mathematical calculation, using a logarithmic regression, makes it possible to determine the dose of LMWF required to decrease the weight of the control thrombi by 80% (ED 80). Thus, the ED 80 for the LMWF, given subcutaneously, is 7.4 (5.6–9.8) mg/kg.

As observed by Millet et al., 1999 (ibid) on the low molecular weight fucan obtained by acid hydrolysis, and taking Fragmin® as the reference product, the LMWF shows, in rabbits, earlier and longer-lasting kinetics of antithrombotic activity.

3. Arteriovenous Thrombosis According to Umetsu in Rabbits 3-a: Antithrombotic Activity Intravenously Protocol The animals used are homozygous New Zealand male rabbits weighing on average 2 to 2.5 kg. After a 6-day period of stabilization of the animals in an animal house, they are used during a period of fasting.

After premedication of the animals with Imalgene®, they are anesthetized by intravenous injection of 1% sodium pentobarbital into the marginal ear vein. The injection is given slowly with the pupil reflex and respiration being monitored. Approximately 4 to 5 ml of pentobarbital are injected into a rabbit weighing 2 kg.

A carotid artery and an opposite jugular vein are freed. An arteriovenous shunt is placed between these two vessels. This shunt is composed of 2 polyethylene catheters (outside diameter 1.9 mm) 12.5 cm in length, these two catheters being connected to one another via a third catheter, which has an internal diameter of 1.57 mm and is 6 cm in length, inside which is placed a silk thread.

The catheters are siliconized (Sigmacote®, Sigma). A Doppler ring 1.3 mm in diameter is fixed around the catheter introduced into the carotid in order to assess the variation in blood flow velocity, representative of the occlusion.

A first group of rabbits, which will be used as a control, receives physiological saline, three other groups receiving, respectively, a solution of NFH (1 mg/kg) and two solutions of LMWF (1 mg/kg and 2 mg/kg). The various solutions and their solvents (the physiological saline) are administered in a volume of 1 ml/kg, by intravenous injection into a marginal ear vein (on the opposite side to that being used to maintain the anesthesia of the animal), 5 minutes before creating the thrombogenic situation.

Results

Table II summarizes the occlusion times (in minutes) as a function of the doses of LMWF and of NFH administered intravenously. The symbol *** indicates the threshold of significance of a probability equal to or less than 0.1% (p≦0.001 in the statistical Student's test).

TABLE II

|  | Control | NFH 1 mg/kg | LMWF 1 mg/kg | LMWF 2 mg/kg |
|---|---|---|---|---|
| Occlusion time (min.) | 15.6 ± 1.7 | 55.4 ± 2.9*** | 27.6 ± 6.5 | 43.7 ± 6.0*** |
| Number of animals | 9 | 5 | 7 | 6 |

It emerges from these results that the LMWF, administered intravenously in the Umetsu model adapted to rabbits, has arterial antithrombotic activity at doses close to those responsible for venous antithrombotic activity.

Doubling of the occlusion time is noted 5 minutes after intravenous administration of LMWF at a dose of 1 mg/kg (dose close to the venous antithrombotic ED 80). The NFH administered at a dose of 1 mg/kg, under the same conditions, increases close to 4-fold the time required to obtain complete vascular obstruction in the control animals. Moreover, it should be noted that this dose corresponds to 10 times the venous antithrombotic ED 80 for the NFH.

3-b: Antithrombotic Activity Subcutaneously

Protocol

The protocol as indicated above is carried out, the various solutions and their solvents (the physiological saline) being administered in a volume of 1 ml/kg, subcutaneously, 2 hours being creating the thrombogenic situation. The animals are divided into three groups: a first group, which will be used as a control, receives physiological saline, whereas the other groups receive, respectively, solutions of LMWF at a dose of 7.5 mg/kg and of LMWH at a dose of 60 IU anti-Xa/kg.

Results

Table III summarizes the occlusion times (in minutes) as a function of the doses of LMWF and of LMWH administered subcutaneously.

TABLE III

|  | Control | LMWH (60 IU anti-Xa/kg) | LMWF (7.5 mg/kg) |
|---|---|---|---|
| Occlusion time (min.) | 12.6 ± 1.0 | 11.8 ± 1.3 | 22.8 ± 3.4 |
| Number of animals | 5 | 4 | 4 |

It emerges from these results that, at the doses tested, given subcutaneously, the LMWF doubles the control occlusion time, whereas the LMWH has no effect.

Contrary to that which is noted for the NFH (by intravenous injection) and for the LMWH (subcutaneous injection), the dose of LMWF required to double the arterial occlusion time is very close to the venous antithrombotic ED 80 (namely 7.4 mg/kg), unlike the heparins, for which it is necessary to multiply the venous antithrombotic dose close to 10-fold in order to obtain a dose which is active in arterial thrombosis.

4. Arterial Thrombosis With $FeCl_3$ in Rats

Protocol

Only intravenous administration was studied in this model.

The animals used are male Wistar rats weighing from 240 to 390 g. After a 6-day period of stabilization of the animals in an animal house, they are used in a period of fasting.

After anesthesia with 15% ethyl carbonate (10 ml/kg; Prolabo, Paris, France), a carotid artery is exposed and surrounding tissues or nerves are cleared, and a square of parafilm is placed under the carotid. A Doppler probe is placed around the carotid (cephalic side). The Doppler signal is adjusted so as to have a deflection which is maximal and assimilated to a value of 100%.

After a period of stabilization of the blood flow, a disc (3 mm in diameter) of Whatman filter paper is placed on the carotid, distally to the probe. Two microliters of a solution of $FeCl_3$ (Osi, Paris, France) at 25% in 1 M hydrochloric acid are deposited on to the filter paper, which is then placed vertically to the parafilm in contact with the cleared carotid. A timer is started. After 30-second contact of the filter paper, this is removed. The formation the thrombus is then monitored by analyzing the Doppler signal.

Evaluation of the thrombosis, expressed in minutes, consists in measuring the period of time which separates the application of the $FeCl_3$ from the time at which the Doppler signal reaches the base line, thus reflecting total occlusion.

The animals are divided up into three main groups, one receiving the physiological saline (control group) and the others receiving, respectively, the LMWF (at doses ranging from 1.25 to 10 mg/kg) and the NFH (at the doses of 1.25 and 2.5 mg/kg). The physiological saline, and also the solutions of LMWF and of NFH, are injected intravenously, in a volume of 1 ml/kg, 5 minutes before inducing the thrombosis.

Results

Table IV summarizes the arterial occlusion times (in minutes) and also the multiplication factor for the occlusion time (calculated relative to the control occlusion time), as a function of the doses of LMWF and of NFH administered intravenously. The symbols * and  indicate the thresholds of significance of a probability equal to or less than 0.1% and 1%, respectively ($p \leq 0.001$ and $p \leq 0.1$, respectively, in the statistical Student's test).

TABLE IV

|  | Occlusion time (min.) | Multiplication factor | Number of animals |
|---|---|---|---|
| Control | 11.6 ± 0.58 | / | 19 |
| LMWF: |  |  |  |
| 10 mg/kg | 52.5 ± 7.5*** | 4.52 | 6 |
| 5 mg/kg | 41.7 ± 8.9*** | 3.59 | 7 |
| 2.5 mg/kg | 31.9 ± 9.3** | 2.75 | 6 |
| 1.25 mg/kg | 12.7 ± 1.4 | 1.09 | 5 |
| NFH: |  |  |  |
| 2.5 mg/kg | 60.0 ± 0*** | 5.17 | 2 |
| 1.25 mg/kg | 20.5 ± 0.5** | 1.76 | 3 |

As shown in the table above, the occlusion time is 20.5 minutes after an injection of NFH at a dose of 1.25 mg/kg and 60 minutes when the NFH is administered at a dose of 2.5 mg/kg, i.e. more than 5 times the control time.

With regard to the LMWF, it has a significant dose-dependent activity. From the dose of 2.5 mg/kg, the injection of LMWF induces a significant delay in the arterial occlusion time, this time being more than doubled compared to the control time.

A mathematical calculation (linear regression) makes it possible to deduce from the results above the doses of LMWF and of NFH required to double the arterial occlusion time, which are close to 2 mg/kg for the LMWH and to 1.25 mg/kg for the NFH.

EXAMPLE 2

Hemorrhagic Risk and Anticoagulant Effect of Sulfated Polysaccharides Obtained by Depolymerization of a Fucan From Phaeophyceae 1. Hemorrhagic Risk in Rabbits a) Materials and Methods In rabbits, the hemorrhagic risk of the LMWF and of the LMWH is evaluated by measuring prolonging of bleeding times, according to the model of Carter et al. modified by Doutremepuich et al. (Throm. Res., 1979, 15, 581–586), after administration of the products subcutaneously, 2 hours before induction of the hemorrhage, at doses close to the venous antithrombotic ED 80 and 5 times this dose.

The low molecular weight fucan (LMWF) and the animals used are identical to those described in Example 1. In the case of the injection at 1×ED 80, the low molecular weight heparin (LMWH) is Fragmin® as described in Example 1; in the case of the injection at 5×ED 80, it is Tinzaparin® (10,000 IU anti-Xa/0.5 ml; batch Q 6369B) supplied by the company Innohep (France).

b) Results

At the dose which allows doubling of the control arterial occlusion time, corresponding to the venous antithrombotic ED 80, the LMWF and LMWH administered subcutaneously have no hemorrhagenic activity. It is also noted that, at this dose, and unlike the LMWF, the LMWH is inactive in rabbits in the model of arterial thrombosis according to the Umetsu model.

At 5 times this dose, neither the LMWH or the LMWF induces a significant increase in the bleeding time.

2. Hemorrhagic Risk in Rats a) Materials and Methods

In rats, the hemorrhagic risk of the LMWF, of the NFH and of the LMWH is evaluated by measuring the increase in the bleeding times, according to the model of Dejana et al. (Throm. Haemost., 1982, 48, 108–111). The LMWF, the NFH and the animals used are identical to those described in Example 1.

The compounds are administered intravenously at doses of 5 and 10 mg/kg for the LMWF (doses corresponding, respectively, to 2.5 times and to 5 times the dose which doubles the control occlusion time (OT) (cf. Table IV), of 750 and 1500 IU anti-Xa/kg for the LMWH (Fragmin®) and of 1 mg/kg for the NFH, 5 minutes before induction of the hemorrhage.

b) Results

Table V summarizes, as percentages, the increase in the bleeding times obtained.

TABLE V

| Doses | Products | Increase in the bleeding times | Number of animals |
|---|---|---|---|
| 1 × OT × 2 | LMWF | nd* | |
| | NFH | >80% | 9 |
| 2.5 × OT × 2 | LMWF | >50% | 8 |
| | LMWH | >200% | 8 |
| 5 × OT × 2 | LMWF | >200% | 3 |
| | LMWH | >200% | 3 |

*nd: not determined

It emerges from this table that, at 2.5 times the dose required to double the control occlusion time, the LMWF clearly increases the bleeding time less than the LMWH. At 5 times this dose, the increases in the bleeding times are similar for the two products.

Thus, in comparison to an NFH and to an LMWH, it emerges from Table V that the LMWF presents a moderated hemorrhagic risk.

3. Anticoagulant Effect ex Vivo a) Materials and Methods

Plasmas are used which originate:

from rabbits in which a venous thrombosis according to the Wessler model has been induced;

from the rats used in the arterial thrombosis experiment according to Example 1, these rats having received, intravenously, doses close to that required to double the control occlusion time, namely 2.5 mg/kg of LMWF or 1.25 mg/kg of NFH, or double doses, i.e. 5 mg/kg of LMWF or 2.5 mg/kg of NFH.

Injection of a physiological saline solution is used as a control. The animals' plasma is taken just after the formation of the venous sac.

The activated partial thromboplastin time (APTT or KCT) is measured in the following way:

for the plasmas taken from rabbits, 100 µl of plasma and 100 µl of CKPrest reagent (Stago, Asnières, France) are incubated for 3 minutes at 37° C., and then 100 µl of $CaCl_2$ are added to trigger clotting. A measurement of the KCT (Kaolin Cephalin Time) is thus obtained;

for the plasmas taken from the rats, the APTT is measured on the ACL 3000 automat (Delhomme, Paris, France). 53 µl of plasma and 53 µl of cephalin activated with ellagic acid (provided by IL, Paris, France, under reference 97570-10) are brought into contact with one another, after incubation at 37° C. Clotting is triggered by adding 53 µl of $CaCl_2$. The increase in turbidity due to the formation of the fibrinous clot is detected by nephelometry.

The thrombin time (TT) is measured in the following way;

for the plasmas taken from the rabbits, 100 µl of thrombin (human thrombin supplied by Fibrindex Ortho Diagnostic Systeme, Roissy, France) are mixed together with 200 µl of plasma, after incubation for 2 minutes at 37° C. The addition of the thrombin to the plasma triggers the fibrin clot formation process;

for the plasmas taken from the rats, the TT is measured on the ACL 3000 automat described above.

The plasma and the human thrombin (reference 0880, Stago, Asnieres, France), after incubation at 37° C., are brought into contact with one another volume for volume (75 µl). The formation of a fibrin clot increases the turbidity, which is detected by nephelometry on the clotting automat.

b) Results

Anticoagulant Effect in Rats (Administration of the Compounds Intravenously)

In rats, intravenous injection of LMWF significantly prolongs the APTT and the TT, but clearly less than that which is observed with the NFH.

Anticoagulant Effect in Rabbits (Administration of the Compounds Subcutaneously)

The results of the KCTs obtained in rabbits, expressed in seconds, are summarized in Table VI below. The symbols * and ** indicate the thresholds of significance of a probability equal to or less than 5% and 1%, respectively ($p \leq 0.05$ and $p \leq 0.01$, respectively, in the statistical Student's test).

TABLE VI

| | Dose | KCT (seconds) | Number of animals |
|---|---|---|---|
| Control | 0 | 25.1 ± 1.3 | 8 |
| LMWF | 7.5 mg/kg | 28.2 ± 1.8 | 6 |
| | 10 mg/kg | 29.4 ± 1.5* | 7 |
| LMWH | 50 IU anti-Xa/kg | 25.7 ± 1.7 | 3 |
| | 100 IU anti-Xa/kg | 27.0 ± 1.5 | 3 |
| | 200 IU anti-Xa/kg | 33.9 ± 5.0** | 3 |

It emerges from Table VI that the LMWH (Fragmin®), administered at doses ranging from 50 to 200 IU anti-Xa/kg, 2 hours before the blood samples are taken, does not a significant increase in the KCT except at a very high dose (200 IU anti-Xa/kg) (35.3% increase compared to the control group).

The KCT undergoes no significant modification for a dose of LMWF of 7.5 mg/kg, administered subcutaneously 2 hours before the blood samples are taken. At a dose of 10 mg/kg, a slight but significant increase is noted (17% increase)

The results of the TTs obtained in rabbits, expressed in seconds, are summarized in Table VII below. The symbol ** indicates the threshold of significance of a probability equal to or less than 1% ($p \leq 0.01$ in the statistical Student's test).

TABLE VII

| | Dose | TT (seconds) | Number of animals |
|---|---|---|---|
| Control | 0 | 31.6 ± 1.3 | 9 |
| LMWF | 7.5 mg/kg | 34.7 ± 2.2 | 6 |
| | 10 mg/kg | 31.5 ± 1.2 | 7 |
| LMWH | 50 IU anti-Xa/kg | 32.5 ± 2.7 | 3 |
| | 100 IU anti-Xa/kg | 38.2 ± 4.1 | 3 |
| | 200 IU anti-Xa/kg | >98** | 3 |

It emerges from Table VII that the mean thrombin time (TT) undergoes no significant modification for the doses of LMWF tested, administered subcutaneously 2 hours before the blood samples are taken. It is noted that the LMWH (Fragmin®), at the doses tested, increases the TT.

EXAMPLE 3

Ex Vivo Study of the Effect of Sulfated Polysaccharides Obtained by Radical Depolymerization of a Fucan From Phaeophyceae on Platelet Aggregation a) Materials and Methods The LMWF and the NFH are as described in Example 1. The LMWH is Tinzaparin®, supplied by Innohep.

In Rabbits

The LMWF and the LMWH are injected, subcutaneously, at a dose close to 5×ED 80 (5 times the dose required to decrease the mean weight of the control thrombi by 80%) determined according to the venous thrombosis model according to Wessler (ED 80 of Tinzaparin® by subcutaneous injection: 80 IU anti-Xa/kg). Thus, the LMWF and the LMWH are injected, at the respective doses of 37.5 mg/kg and 400 IU anti-Xa/kg. With regard to the NFH, it is administered intravenously at a dose close to 10×ED 80, i.e. at 1 mg/kg.

Aggregation With Thrombin

Bovine thrombin at 100 U NIH (National Institute of Health)/ml (Sigma, reference 4648), stored at −70° C., is thawed and diluted to 1/10 in physiological saline, and then kept in ice throughout the experiment. 100 µl of PBS buffer and an amount of thrombin (amount close to 8 µl) necessary to have a final concentration close to 0.2 U NIH/ml are added to 300 µl of PRP (Platelet-Rich Plasma), obtained by centrifuging the animals' blood for 10 minutes at 400 g, which have been preincubated for 1 minute at 37° C.

Aggregation with ADP (Adenosine Diphosphate)

A 100 µM ADP solution (reference 0494, Stago, Asnieres, France), stored at −20° C., is thawed, diluted to 1/25 and 1/12.5 in Tyrode's solution containing calcium (138.6 mM NaCl; 2.8 mM KCl; 11.9 mM $NaHCO_3$; 1.1 mM $MgCl_2$; 0.33 mM $NaH_2PO_4$; 11.2 mM glucose; 4 µM $CaCl_2$; FOURNIER Laboratories) and placed in ice throughout the experiment. After incubation of 300 µl of PRP at 37° C. for 1 minute, the platelet aggregation is triggered with 100 µl of a solution of ADP (final concentration of 1 and 2 µM).

In Rats

The LMWF and the NFH are injected intravenously, 5 minutes before the blood samples are taken, at the respective doses of 2.5 and 5 mg/kg for the LMWF and of 1.25 and 2.5 mg/kg for the NFH.

The platelet aggregation protocols are similar to those described above, except for the following differences for the protocol for aggregation with thrombin: the buffer added to the PRP is a recalcified Tyrode's buffer, and the final concentration of thrombin is 0.6 U NIH/ml.

b) Results

In Rabbits

The LMWF and the LMWH (at the dose of 5×ED 80) and the NFH (at the dose of 10×ED 80) inhibit the thrombin-induced platelet aggregation at 100%, but do not inhibit the platelet aggregation induced with 1 µM and 2 µM of ADP.

In Rats

The LMWF and the NFH inhibit the thrombin-induced platelet aggregation at 100%. Contrary to that which is noted following the injection of NFH (lack of inhibition or very weak inhibition of platelet aggregation), the LMWF, whatever the dose injected, decreases the ADP-induced platelet aggregation by 35 to 45%, without it being possible to observe a dose-effect.

EXAMPLE 4

In Vivo Study of the Effect of Sulfated Polysaccharides Obtained by Radical Depolymerization of a Fucan from Phaeophyceae on the Prevention of Arterial Restenosis The treatment of arterial stenoses via the endovascular route is a technique which is common practice. It consists in introducing into the artery a balloon which is expanded against the stenosis (angioplasty operation) with the aim of restoring a normal vascular caliber. The angioplasty is most commonly followed by the insertion of a stent which makes it possible, due to its radial expansion strength, to maintain the caliber of the artery. This technique is frequently used in the treatment of coronary, iliac or renal atheromatous stenoses. The parietal trauma induced by the angioplasty and the insertion of a stent is, unfortunately, responsible for a restenosis of the vessel in 20 to 30% of cases in humans. This restenosis is largely due to proliferation and migration of the smooth muscle cells (SMCs) from the media to the intima of the vessel. The appearance of neointimal hyperplasia reduces the caliber of the stent, promotes downstream ischemia and is the cause, in humans, of not insignificant morbidity and mortality.

Fractions of sulfated polysaccharide which can be obtained by radical depolymerization of a crude fucan derived from Phaeophyceae, said polysaccharide having a molar mass of less than or equal to 10,000 g/mol, may be used, in accordance with the invention, to prevent arterial restenosis, as demonstrated below in a model of restenosis in rabbits, in the iliac artery.

a) Materials and Methods

The animals are New Zealand rabbits weighing on average 3.5 to 4 kg. They are anesthetized with pentobarbital.

10 iliac stents are implanted in 5 rabbits. A stent is positioned in each iliac artery (approach via the carotid). The insertion of each stent is preceded by 3 angioplasties of one minute at 10 atmospheres (atm) The stent is inserted under a pressure of 10 atm for 30 seconds.

The animals are then treated for 14 days with the LMWF obtained in Example 1, injected intramuscularly twice a day at the dose of 10 mg/kg/24 h. The control group consists of 6 stented arteries in 3 rabbits. After 14 days, the animals are sacrificed. The lower abdominal aorta and the iliac arteries are removed and are fixed under pressure (in formol) and embedded in methacrylate. Sections are then cut on a microtome in order to carry out histological and histomorphometric analyses, and to calculate the surface area of the arteries.

b) Results

The surface area measurements carried out (intima, media, and intima/media and intima/internal elastic lamina ratios), given in Table VIII (in which "n" represents the number of measurements made), indicate a decrease in the intimal hyperplasia in the group of animals treated with the LMWF. This decrease in the intimal hyperplasia is very large (about 60%).

It should also be noted that, beyond the decrease in the surface area of the intima and in the intima/media and intima/internal elastic lamina ratios, the fucan has no effect on the surface area of the media, which reveals an inhibition specific for the SMC proliferation.

TABLE VIII

|  | Control (n = 6) | Animals treated with the LMWF (n = 10) | Decrease (%) |
|---|---|---|---|
| Intima | 1.83 | 0.73 | 60 |
| s.d. | 0.51 | 0.20 | |
| Media | 0.41 | 0.37 | n.s. |
| s.d. | 0.02 | 0.19 | |
| Intima/media | 4.48 | 1.97 | 56 |
| s.d. | 1.47 | 0.65 | |
| Intima/IEL | 0.35 | 0.17 | 52 |
| s.d. | 0.08 | 0.06 | | s.d. = standard deviation
n.s. = not significant
IEL = internal elastic lamina

As emerges from the above, the invention is in no way limited to its methods of implementation, preparation and application which have just been described more explicitly; on the contrary, it encompasses all the variants which may occur to a person skilled in the art, without departing from the context or scope of the present invention.

What is claimed is:

1. A method for preventing or treating vascular thrombosis, which comprises administering to a subject a medicinal product comprising a sulfated polysaccharide obtained by radical depolymerization of a crude fucan derived from Phaeophyceae, said polysaccharide having a molar mass of less than or equal to 10,000 g/mol.

2. The method as claimed in claim 1, wherein venous thrombosis is treated or prevented.

3. The method as claimed in claim 1, wherein arterial thrombosis is treated or prevented.

4. The method as claimed in claim 3, wherein arterial restenosis is prevented.

5. The method as claimed in claim 1, wherein said sulfated polysaccharide has a molar mass of less than 5000 g/mol.

6. The method as claimed in claim 1, wherein said medicinal product is administered parenterally.

7. The method as claimed in claim 6, wherein said medicinal product is administered intravenously.

8. The method as claimed in claim 6, wherein said medicinal product is administered subcutaneously.

9. The method as claimed in claim 8, wherein said medicinal product is administered, preventatively, at a daily dose of between 150 and 300 mg.

10. The method as claimed in claim 8, wherein said medicinal product is administered, curatively, at a daily dose of between 450 and 600 mg.

11. The method as claimed in claim 4, wherein said medicinal product is administered locally.

12. The method as claimed in claim 11, wherein said medicinal product is administered by endoparietal diffusion.

* * * * *